(12) United States Patent
Bastia

(10) Patent No.: US 11,793,417 B2
(45) Date of Patent: Oct. 24, 2023

(54) APPARATUS AND A METHOD OF MEASUREMENT THEREOF

(71) Applicant: THD S.P.A., Correggio (IT)

(72) Inventor: Filippo Bastia, Soliera (IT)

(73) Assignee: THD S.P.A., Correggio (IT)

( * ) Notice: Subject to any disclaimer, the term of this patent is extended or adjusted under 35 U.S.C. 154(b) by 540 days.

(21) Appl. No.: 15/151,965

(22) Filed: May 11, 2016

(65) Prior Publication Data
US 2016/0338605 A1 Nov. 24, 2016

(30) Foreign Application Priority Data

May 20, 2015 (IT) .................... 102015000016064

(51) Int. Cl.
*A61B 5/03* (2006.01)
*A61B 5/00* (2006.01)
*A61B 5/22* (2006.01)

(52) U.S. Cl.
CPC .............. *A61B 5/036* (2013.01); *A61B 5/227* (2013.01); *A61B 5/4255* (2013.01); *A61B 5/7475* (2013.01); *A61B 5/037* (2013.01); *A61B 5/742* (2013.01); *A61B 2562/168* (2013.01)

(58) Field of Classification Search
CPC ....... A61B 5/036; A61B 5/227; A61B 5/4255; A61B 5/7475
USPC ........................................................ 600/561
See application file for complete search history.

(56) References Cited

U.S. PATENT DOCUMENTS

| 4,782,817 A * | 11/1988 | Singh ..................... A61M 60/50 600/17 |
| 5,003,637 A * | 4/1991 | Lonon ................ A41D 19/0024 2/160 |
| 6,449,571 B1 * | 9/2002 | Tarig ..................... G01F 1/6965 137/486 |
| 7,947,001 B1 | 5/2011 | Sarvazyan |
| 2007/0213656 A1 | 9/2007 | Ferdinand |

(Continued)

FOREIGN PATENT DOCUMENTS

| CN | 1423540 A | 6/2003 |
| CN | 103347443 A | 10/2013 |

(Continued)

*Primary Examiner* — Daniel L Cerioni
(74) *Attorney, Agent, or Firm* — Pearne & Gordon LLP; J. Gregory Chrisman

(57) ABSTRACT

An apparatus (1) for performing manometric measurements by way of medical devices of the pneumatic type, comprises a processing unit (10), and a pressure transducer (4), which is connected to the unit (10) and adapted to be fluid-dynamically connected to the pneumatic device (3).
The processing unit (10) comprises: a setting module (11) configured for setting a reference parameter, which is a function of conformational and/or dimensional features of the device (3); and a measurement module (12) configured for processing the measurements made by the transducer (4), according to the reference parameters (a, b, c) which were set for calculating respective objective pressure values.
The medical device (3) of the pneumatic type is fluid-dynamically connectable to a measurement apparatus (1), which is provided with an hollow and compressible active portion (30) and provided with an internal fluid-dynamic path adapted to put into communication the apparatus (1) with the cavity of the active portion (30).

5 Claims, 3 Drawing Sheets

(56) References Cited

U.S. PATENT DOCUMENTS

| | | | |
|---|---|---|---|
| 2012/0016215 A1* | 1/2012 | Condurso | A61B 5/021 600/316 |
| 2013/0253377 A1 | 9/2013 | Lin et al. | |
| 2013/0310710 A1 | 11/2013 | Eswaran et al. | |
| 2014/0213927 A1* | 7/2014 | Webster | G01K 1/024 600/549 |
| 2016/0338605 A1 | 11/2016 | Bastia | |

FOREIGN PATENT DOCUMENTS

| | | |
|---|---|---|
| CN | 107743375 A | 2/2018 |
| FR | 2790379 A1 | 9/2000 |
| GB | 2318513 A | 4/1998 |
| JP | 2007206000 A | 8/2007 |
| TW | 201338759 A | 10/2013 |

* cited by examiner

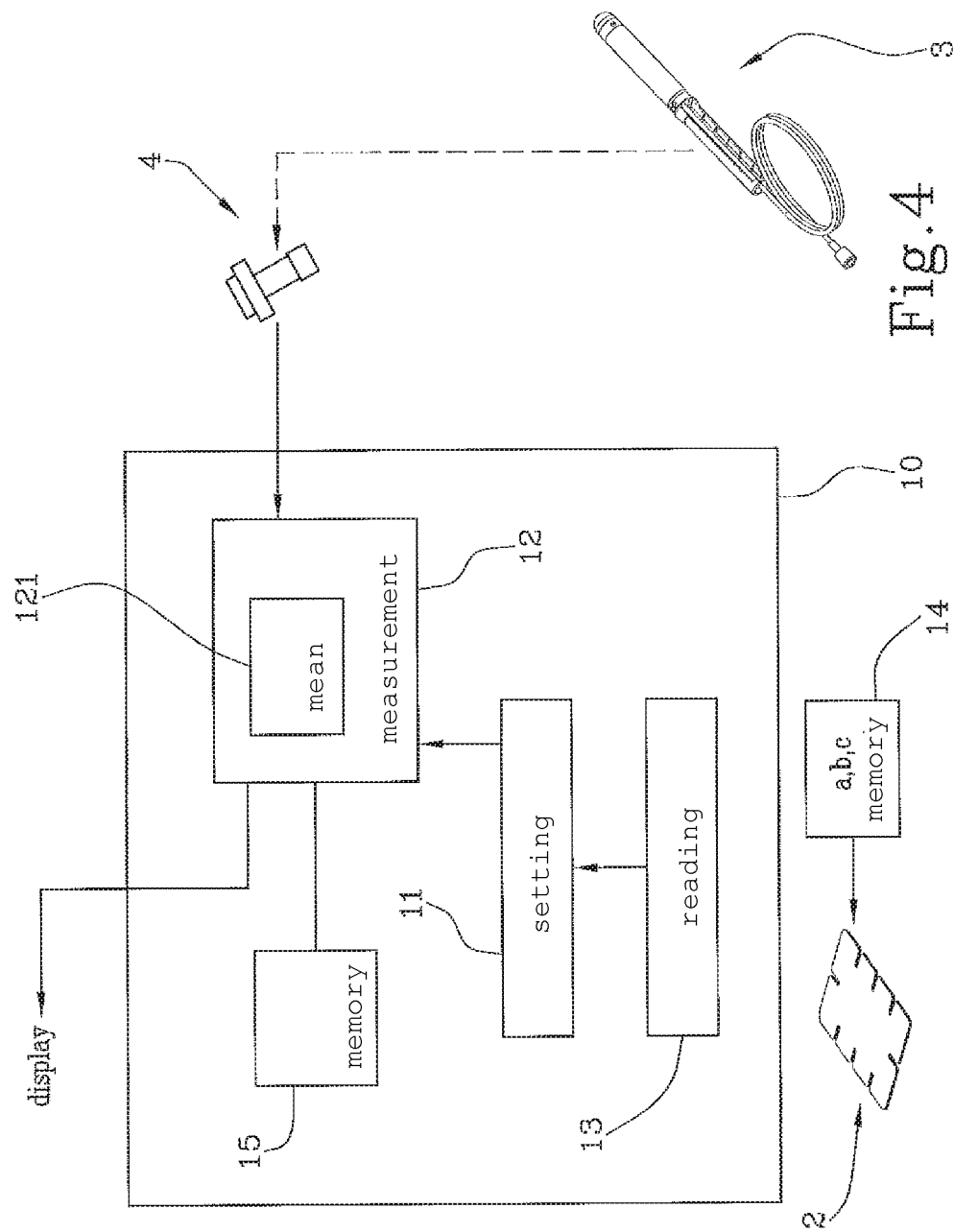

APPARATUS AND A METHOD OF MEASUREMENT THEREOF

The present invention has for object an apparatus and a method for performing manometric measurements by way of medical devices of the pneumatic type.

The invention is devised to be particularly, but not exclusively, employed in anorectal clinical examinations, with particular reference to anorectal manometry.

At present, different types of examinations are performed for clinically evaluating the state of health of the anal sphincter, which include the manometric measurement being aimed at evaluating capability of the sphincter muscles to exert sufficient clamping pressure to hold solids, liquids and gases.

The manometric measurement is carried out via probes that are introduced into the anal canal.

One type of probe used in this field operates pneumatically and, according to the compression exerted by the anal canal on the probe itself, one can determine retention capacity of the sphincter.

One of the current drawbacks of measurement systems is constituted by the fact that the pressure values detected are meaningful only in relation to the specific probe used, the specific conditions of calibration of the probe and the circumstances in which the examination is effected.

Thus the results obtained depend both on how calibration is performed, which requires considerable expertise on the part of the surgeon, as well as on the type of apparatus used, which introduces its own load loss as well as diversified load losses between an apparatus and the other.

This implies that the results obtained are not comparable and that therefore cannot be used effectively on a scientific level.

In this context, the technical task underlying the present invention is to propose a system and a method of measurement which overcome the drawbacks of the prior art.

The technical task mentioned is attained by the system and method of measurement implemented respectively in accordance with claim 1 and claim 18.

Further characteristics and advantages of the present invention will become more apparent from the indicative, and therefore non-limiting description of a preferred but non-exclusive embodiment of the method of measurement of the invention, illustrated in the accompanying drawings in which:

FIG. 4 is a schematic representation of the operating modules and the memory module employed in the invention.

Figure 1:
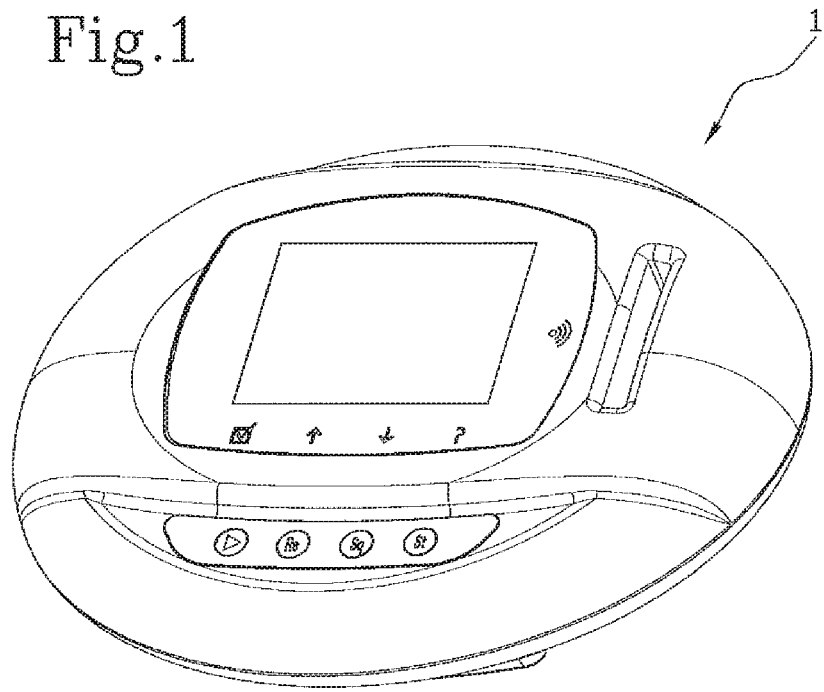
FIG. 1 is an axonometric view of an apparatus comprised in an operative resting configuration thereof according to the invention.

With reference to the attached figures, by the numeral 1 it is indicated the measuring apparatus according to the invention.

The apparatus 1 herein provided was made to perform manometric measurements through the use of medical devices 3 of the pneumatic type.

In particular, the apparatus 1 may be of the type suitable to be used in anorectal clinical examinations, such as anorectal manometry, through use of pneumatic technology-based probes 3.

In the embodiment illustrated in the attached figures, the apparatus 1 is a tester which includes, in addition to its own processing unit 10, the means necessary to the operation of the probe (or other device), a protective casing, any feeding means, means of user interface, such as display or the like, and so on.

The medical device 3 is preferably provided with a compressible hollow portion 30, or "active portion", and can be connected to the apparatus 1 by means of a Luer-Lock fitting 31.

Essentially, during the diagnostic test, the active portion 30 is compressed by the anorectal muscles; in this manner, measurements on the examined muscle tone can be performed.

According to an important aspect of the invention, the proposed apparatus 1 includes a pressure transducer 4 connected to the processing unit 10, which pressure transducer 4 is capable of being fluid-dynamically connected to the device 3.

In detail, the pressure transducer 4, in use, is preferably in fluid communication with the interior of the cavity of the active portion 30 of the device 3; this aspect will be discussed in more detail in a later section.

In general, it should be appreciated that the processing unit of the present description is disclosed as divided into distinct functional modules in order that features thereof can be described in a clear and complete manner.

In practice, this processing unit 10 may be constituted by a single device, an apparatus or an electronic system suitably programmed to perform the functions described above.

The various modules may correspond to hardware entity and/or software routines.

Alternatively or in addition, such functions can be performed by a plurality of electronic devices, whereon aforesaid functional modules can be distributed.

In general, the processing unit 10 may use one or more microprocessors or microcontrollers or the like for executing the instructions contained within the memory modules.

The processing unit 10 of the invention includes a setting module 11 configured for setting one or more reference parameters a, b, c. By the wording "setting of parameters", it is meant the acquisition or selection of these reference parameters a, b, c for the purposes of proper execution of manometric measurements.

Prior to performing each single examination session, the parameters a, b, c are preferably acquired from time to time; alternatively such parameters a, b, c can be preset and for example be comprised within a finite parameters set which is pre-registered on a memory module 15.

Setting of the parameters a, b, c may be performed by the user by way of external means 2 or by way of an interface that is predisposed on the apparatus 1, such as keypads, touch screen display, etc.

At least one of the reference parameters a, b, c is a function, at least, of conformational and/or dimensional features of the anorectal probe 3 (or other device) or other physical features thereof.

The processing unit 10 then includes a measurement module 12 configured to process the measurements made by said transducer 4 according to the established reference parameters a, b, c, thereby calculating respective objective values of pressure.

In practice, as it appears clear from the discussion that follows, the invention advantageously allows to make manometer measurements independent of the characteristics of the medical device 3, the behavior of the transducer 4 and in general the circumstances based on which the measurements takes place.

In this way, the invention is able to return the values of the pressures measured by means of the device 3, which are substantially equal to the real value that was applied to the device 3 itself (for example corresponding to the compression of anorectal muscles during the clinical examination).

In this manner, the data collected on the basis of the manometry examinations effected according to the invention, are objective, thus comparable, in that such data neither depend on the physician who performs clinical investigations, nor on the specific setting of a particular device 3.

In detail, the pressure values arising from the invention correspond to the stresses endured by said active portion of the device 3.

In the case where the device is an anorectal probe 3, the active portion 30 is the one intended to be fully introduced into the anorectal canal.

Prior to explaining further aspects concerning the configuration of the processing unit 10, a preferred version of the pneumatic device 3 is herein illustrated, which is intended for use with the proposed apparatus 1.

As anticipated, the device 3 is provided with an active hollow and compressible portion 30 (see FIG. 3), which is provided with a variable internal volume and an internal fluid-dynamic path, preferably at a constant internal volume, arranged to put the cavity of the active portion 30 in communication with the apparatus 1.

In practice, the internal path is formed by conduits arranged internally of the probe and by any cannulas or flexible hoses that terminate in the Luer-Lock connector 31 mentioned above, which cannulas or flexible hoses allow a fluid communication with the interior of the apparatus 1.

The apparatus 1 in turn comprises its own fluid-dynamic path that starts from the entry to which the connector of the device 3 is coupled, and reaches the transducer 4 comprised within the apparatus 1.

This second path may further include the internal volume of the transducer 4 itself.

In this way, the internal detection means of the transducer 4 communicates with the inner volume of the active portion 30 of the device 3.

Preferably, the active portion 30 comprises inflatable and flexible walls. In this case, the apparatus 1 may include air compression means, such as a micro-compressor, which air compression means is capable of bringing the internal volume of the active portion 30 to a value of initial pressure. Such inventiveness, which shall be detailed upon describing on how the invention operates, allows to have a constant and reliable reference for manometric measurements.

In practice, this initial pressure value, for example equal to 150 mmHg, represents a conventional "zero" of each measurement performed based on the invention.

In the preferred embodiment, the setting module 11 is configured to set at least one reference parameter which is a function of one or more of the following characteristic parameters:
  an internal volume of the cavity of said active portion 30 (also termed hereinafter active volume);
  internal volumes (comprised within the device 3, and/or the apparatus 1, and/or the transducer 4) that communicate with the detecting means inside the transducer 4 and the active portion 30 of the device 3 (which collectively define a passive volume);
  the initial pressure at which the active portion 30 is preliminarily brought; and/or the size and/or the external or internal shape of the device 3.

With reference to the first characteristic parameter listed above, in the case where the active portion 30 of the device 3 is previously brought to said initial pressure, the active volume considered may be the one taken by the active portion 30 once the initial pressure has been reached. Essentially, by providing the measurement module 12 with parameters a, b, c, via the setting module 11, which parameters a, b, c, reflect the characteristics of the probe 3 as well as the examination initial conditions, objective pressure values are obtained in output from the apparatus 1 which go beyond the medical device 3 used by the physician who is performing the examination.

In this manner, the pressure transducer output signals 4, that represent "relative" pressure values, are processed such that "actual" and "objective" values can be obtained therefrom, values that, unless there are any variations falling within negligible error ranges, correspond to the pressures de facto applied on the device 3.

In the preferred embodiment of the invention, the measurement module 12 is configured such that a polynomial formula having as coefficients the already set reference parameters a, b, and c, can be applied to the measurements performed by the transducer 4, that is to say to the relative output signals.

For the sake of clarity, some empirical findings are explained hereinafter that have contributed to the conception of the invention.

The output values of a pressure transducer 4 within a pneumatic measuring system, tipically do not match with the changes in the pressure essentially exerted on a pneumatic device 3.

The physical relationship between pressure and volume is not linear indeed, thus the variation of the volume in the active portion 30 is not linearly matched with the variation of the pressure exerted thereon. Additionally, the measuring system is of the pneumatic type which implies use of a compressible fluid; more specifically, the pressure variation transmitted from the active portion 30 to the transducer 4 does not have a linear path.

Moreover, the transducers 4 have a non-linear behavior internally thereof. Following several tests on the medical device 3 and use of statistical regression methods, it was thus found that the pressure value returned by the transducer 4 exhibits a path which is to be meant as being inverse of a polynomial function having coefficients that are in turn a function of one or more of the characteristic parameters listed above.

Therefore, by applying the polynomial to the results in output from the transducer 4, the behavior of the measuring system is linearized and the objective pressure value is obtained as explained above.

It is noted in particular that, where an anorectal probe 3 is used within the specific measuring range that goes from 0 to 400 mm Hg and corresponds to the range of pressures developed in the anorectal canal, the polynomial to be applied to the signal values in output from the transducer 4, is of the second degree; hence the reference parameters a, b, c which are to be supplied to the measuring module 12 from the setting module 11 are three in number.

From a formal point of view, by calling the measured pressure value (i.e., the value in output from the transducer 4), then in order to obtain the pressure value actually exerted on the active portion 30 of the anorectal probe, the formula $y=ax^2+bx+c$ applies, where a, b and c are the aforementioned reference parameters.

Where a type of probe with different conformational and/or physical features is used for the purposes of measurement, it suffices to set new reference parameters which may be obtained experimentally and are distinctive of that specific type of probe.

This aspect shall be detailed upon explanation on how the invention operates.

A further aspect of the invention is disclosed here below, which is obtained from the trial made on the apparatus 1 and the probe 3 of the invention within the anorectal manometry.

It was found that, where acquisition of reliable and proper resolution pressure measures is to be obtained, the ratio between the active volume and the passive volume is critical.

In fact, the smaller the volume inside the active portion of the probe 3 with respect to the sum of the volumes communicating with the detecting means located internally of the transducer 4 and the active portion 30 of the device 3 (i.e., the passive volume), the lower is the resolution of the measurement taken.

Indeed, when moving along the passive volume, up to the detection means arranged internally of the transducer 4, a variation of the active volume tends to "dilute" owing to the fact that the invention employs a compressible fluid.

It was thus empirically found that for the purposes of obtaining a reliable pressure measurement, the ratio between the active and passive volume shall be preferably comprised between 0.05 and 0.95 and still more preferably be equal to 0.4.

In this case, the reference parameters a, b, c are also a function of this ratio.

Similarly, it was found that the ratio between the active volume, and the sum resulting from the active and passive volume, is comprised between 0.2 and 2.8, and preferably equal to 0.6 in order that a reliable measurement pressure is obtained.

Even in this case, the reference parameters shall be a function also of the relationship defined in the previous paragraph.

In the preferred embodiment of the invention, the measuring module 12 is configured for calculating the objective pressure values with a given frequency, for example 100 times per second.

In practice, the processing unit 10 samples the measured pressure values and provides to record the latter in a memory module 15.

Such samples, from which the value of said initial pressure (if applied) is subtracted, are processed by the measurement module 12 so that a mean value is obtained, for example by applying moving mean methods or other types of statistical methods.

To this end, the measurement module 12 may comprise a mean module 121 that may for example include a low-pass filter; in detail, the filter can be of the IIR type (Infinite Impulse Response).

In one embodiment of the invention, the processing unit 10 comprises reader means 13 connected to the setting module 11 and configured for acquiring the reference parameters a, b, c from the external enabling means 2 associated with the device 3.

In the example illustrated in the figures, the enabling means comprises a card 2 which for example includes a RFID transponder, wherein the reference parameters a, b, and c are stored.

In this case, a card 2 can be made available coupled with the respective medical device 3, for example included in the same package.

Preferably, the enabling means 2 comprises its own memory unit 14 that includes the reference parameters a, b, c.

Where the RFID technology is employed, the memory unit 14 mentioned is the one comprised in said transponder.

In the case in which the enabling means 2 includes the RFID transponder, the reader means 13 are of the type suitable for a contactless reading to radio frequency.

Here below, operation of the invention is disclosed with reference to the case wherein use of anorectal probes 3 is made.

Figure 3:
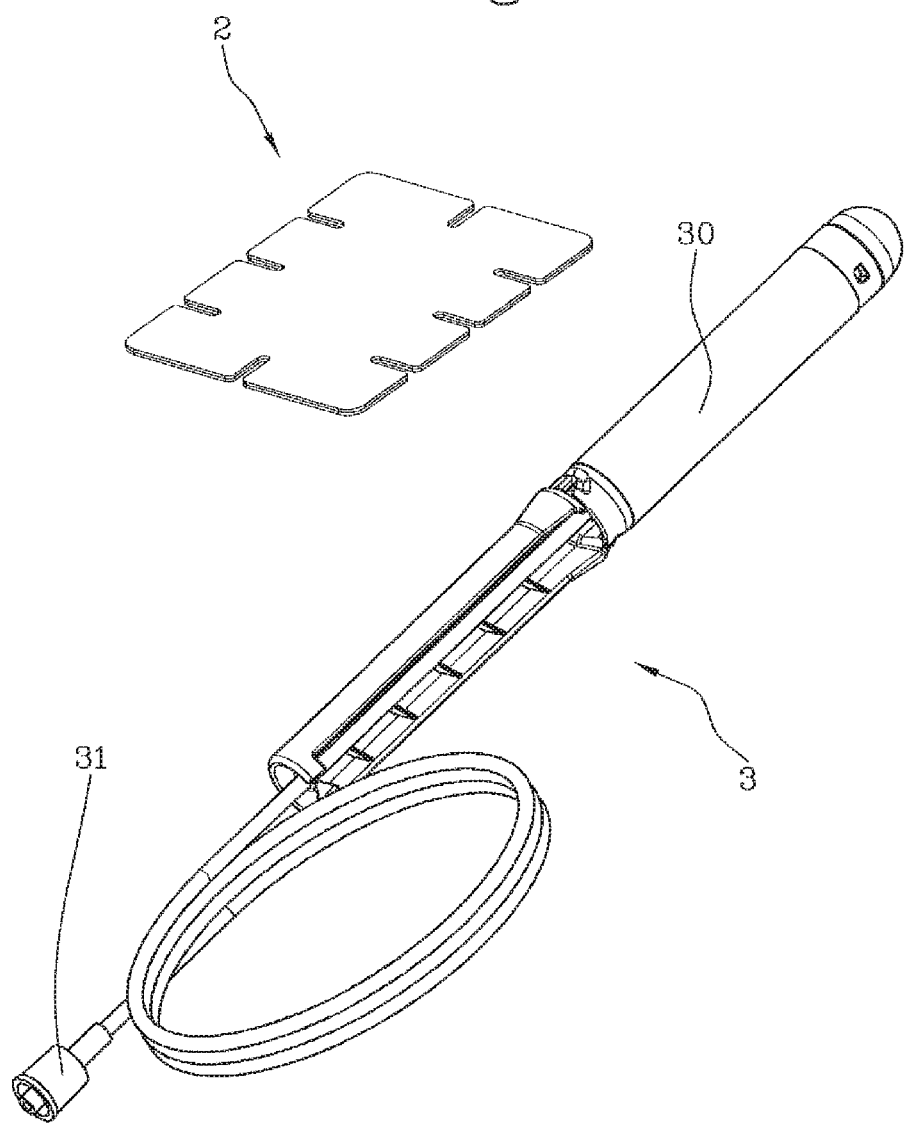
FIG. 3 is an isometric view of a medical device and authorizing means associated therewith.

The physician opens a package including a probe 3 and the card 2, which is uniquely associated to the former (shown by way of example in FIG. 3).

Figure 2:
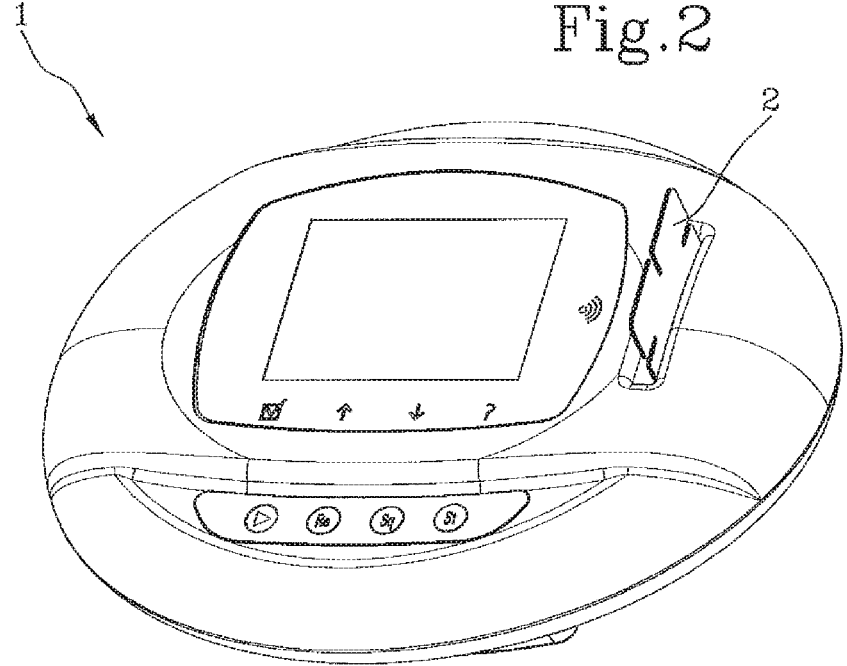
FIG. 2 is the view of FIG. 1, in which the apparatus is associated with authorizing means in an operative activation configuration thereof.

After that, the probe 3 is connected with the apparatus 1 by the physician and the card 2 is placed relative to a tester 1 zone in which the processing unit 10 may read the reference parameters a, b, c recorded in the card 2. In the case represented in FIG. 2, this zone is defined within an insertion slot of the card 2 which is afforded on the casing of the tester 1; this is not a binding arrangement however.

At this point, the active portion 30 of the probe 3 is brought by the physician to said initial pressure, so that a known pressure is set, which is acting as a sure reference for all manometric measurements (i.e., as conventional "zero" as explained above).

In this manner, in order to know the pressure exerted on the probe 3, it will suffice to subtract the known value of the initial pressure from the one determined by the invention.

Note that the transducer 4 of the invention is preferably employed for setting the initial pressure; in this manner, one has the certainty of having brought the active portion 30 at the desired pressure and the invention is thus rendered at least partially free from the pressure change due to height differences of the places in which the clinical examinations are conducted.

At this point, the probe 3 is introduced into the anus of the patient by the physician and the manometric tests are then performed.

Since the processing unit 10 is provided with the reference parameters a, b, c, which are characteristic of that probe or probe model, then the processing unit 10 may process the output signals from the transducer 4 and obtain the pressure actually exerted on the active portion of the probe, so that objective and comparable results are obtained.

Where a second type of probe was used by the physician, the physician would have available a card 2 (or other enabling means) including different value parameters characteristic of that type of device 3.

By recording the new parameters in the processing unit 10 in the manner explained above, one can employ the same apparatus 1 and above all obtain results comparable with those produced through use of the first type of probe, thereby obtaining objective manometric measurements.

The comparability of results is of enormous importance for the purpose of progress in scientific knowledge on the disease and implementation of diagnostic screening.

The invention further consists in a method for performing manometric measurements, with particular reference to anorectal clinical examinations. The proposed method comprises the following steps:

making available a pneumatic device 3 provided with a compressible hollow portion 30 (i.e., the aforesaid active portion);

making available a pressure transducer 4 connectable to the device 3;

setting a reference parameter being a function of an internal volume of said compressible portion 30; and p1 processing the measurements made by the transducer 4 according to preset reference parameters a, b, c, whereby respective objective values of pressure are calculated which correspond to the pressure exerted on the active portion 30.

In the preferred embodiment of the invention the measurements carried out by the transducer 4 are processed according to one or more parameters being a function of one or more of the following variables:

internal volumes communicating with the transducer 4 (or with the detecting means thereof) as well as the active portion 30; the initial pressure at which the active portion 30 is brought preliminarily; the dimensions and/or shapes of the device 3.

It should be appreciated that the functionality of the measuring system which includes the apparatus 1 described above, in particular as defined by the operating and memory modules already mentioned, may correspond to as many actions to be meant as optional steps of the method of the invention.

The proposed method can be implemented by means of a computer program executed on a processing system, which program can be made available on a medium readable by a computer.

The invention claimed is:

1. An apparatus for performing manometric measurements, comprising:
   a processing unit,
   an anorectal probe comprising a hollow and compressible active portion with an internal volume,
   an RFID transponder,
   a reader configured for obtaining a reference parameter via a card associated with the anorectal probe, and
   an apparatus comprising:
      at least one pressure transducer connected to said processing unit and adapted to be fluid-dynamically connected to the anorectal probe, said processing unit comprising:
      at least one setting module comprising computer hardware and/or software; and
      at least one measuring module comprising computer hardware and/or software.

2. The apparatus according to claim 1, further comprising compressor means arranged to be placed in communication with the anorectal probe.

3. The device according to claim 1, in which said active portion exhibits a variable inner volume.

4. The device according to claim 1, wherein said active portion is inflatable.

5. The apparatus according to claim 1, in which the anorectal probe and the card associated with the anorectal probe are both contained within a single package.

* * * * *